United States Patent
Mendelovici et al.

(12)

(10) Patent No.: US 6,677,458 B2
(45) Date of Patent: Jan. 13, 2004

(54) PROCESS FOR THE PREPARATION OF 1,2-BENZISOXAZOLE-3-ACETIC ACID

(75) Inventors: Marioara Mendelovici, Rechovot (IL); Tamar Nidam, Yehud (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 10/090,710

(22) Filed: Mar. 4, 2002

(65) Prior Publication Data

US 2002/0183525 A1 Dec. 5, 2002

Related U.S. Application Data

(60) Provisional application No. 60/273,172, filed on Mar. 2, 2001, and provisional application No. 60/294,847, filed on May 31, 2001, now abandoned.

(51) Int. Cl.$^7$ ............................................. C07D 261/20
(52) U.S. Cl. ....................................................... 548/241
(58) Field of Search ......................................... 548/241

(56) References Cited

U.S. PATENT DOCUMENTS 3,112,199 A  *  11/1963  Camerini et al. ........... 430/490

5,484,763 A     1/1996   Wepplo

FOREIGN PATENT DOCUMENTS

JP       53-77057       8/1978

OTHER PUBLICATIONS

Database CASREACT, Accession No. 110:192693. Thourel et al., "Synthesis of 1,2–benzisooxazole–3–acetic acid–alpha.–14C and–.beta.–14C acid," J. Labelled Compd. Radiopharm. 1988, vol. 25, No. 11, pp. 1235–1244.

* cited by examiner

Primary Examiner—Joseph K. McKane
Assistant Examiner—Golam M M Shameem
(74) Attorney, Agent, or Firm—Kenyon & Kenyon

(57) ABSTRACT

The present invention provides a process for preparing 1,2-benzisoxazole-3-acetic acid, comprising the step of reacting 4-hydroxy-coumarin with hydroxyl-amine in the presence of a base. The present invention further provides a process for preparing a salt of benzisoxazole methane sulfonic acid, comprising the steps of 1) sulfonating 1,2-benzisoxazole-3-acetic acid using chlorosulfonic acid in a solvent mixture comprising methylene chloride and sodium hydroxide; and 2) isolating the salt of benzisoxazole methane sulfonic acid.

16 Claims, No Drawings

PROCESS FOR THE PREPARATION OF 1,2-BENZISOXAZOLE-3-ACETIC ACID

CROSS-REFERENCE TO RELATED APPLICATIONS

This application claims the benefits under 35 U.S.C. §1.119(e) of Provisional Application Ser. Nos. 60/273,172, filed Mar. 2, 2001, and 60/294,847, filed May 31, 2001, now abondoned the disclosure of which is incorporated by reference in its entirety herein.

FIELD OF THE INVENTION

The field of the invention relates to the preparation of 1,2-benzisoxazole-3-acetic acid. Within that field, the present invention relates more particularly to a method for preparing 1,2-benzisoxazole-3-acetic acid comprising the step of reacting 4-hydroxy-coumarin with a hydroxyl-amine in the presence of a base.

BACKGROUND OF THE INVENTION

Zonisamide is currently avaiable as an anti-epileptic agent which possesses anti-convulant and anti-neurotoxic effects. Zonisamide is also known as 1,2-benzisoxazole-3-methane sulfonamide or 3-(sulfamylmethyl)-1,2-benzisoxazole. It has the following chemical formula:

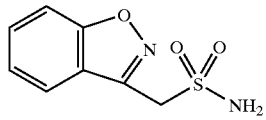

The preparation of zonisamide is described in Japanese Pat. No. 53-77057 and Yakugaku Zasshi, 116(7), 533–47, 1996, both of which are incorporated herein by reference. These references teach a synthesis process of zonisamide that involves 4 or 5-steps, starting from 4-hydroxy-coumarin (4-HC). The synthesis of zonisamide occurs via the intermediates: namely, 1,2-benzisoxazole-3-acetic acid (BOA) and the sodium salt of benzisoxazole methane sulfonic acid (BOS—Na).

Many synthetic routes for preparing zonisamide have been described in the literature. One of the synthetic routes for preparing zonisamide is described in U.S. Pat. No. 4,172,896 and Japanese Pat. No. 53-77057 to Dainnipon. This particular synthetic route starts from 1,2-benzisoxazole-3-bromo-methane (zonisamide-bromide). The zonisamide-bromide is converted to 1,2-benzisoxazole-3-methane-sulfonic acid sodium salt (BOS—Na) in the reaction with sodium sulfite as is shown in the following scheme 1:

Scheme 1

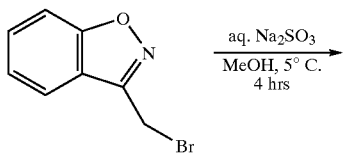

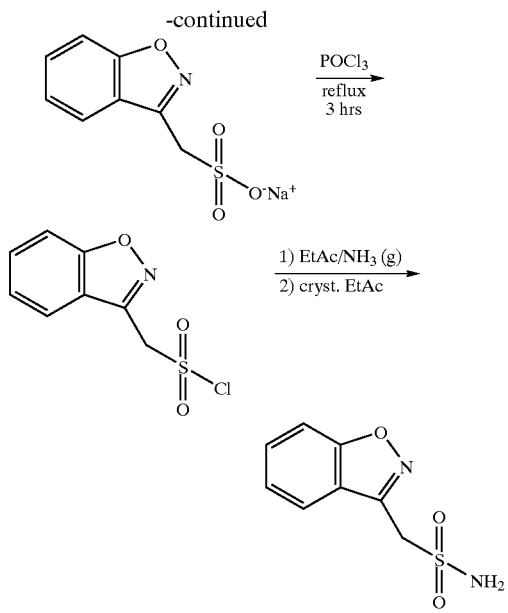

Zonisamide-bromide is prepared according to the literature (Chem. Pharm. Bull., (Tokyo), 24, 632, 1976) by the bromination reaction of 1,2-benzizoxazole-3-acetic acid (BOA). BOA is prepared by Posner reaction (T. Posner, Chem. Ber., 42, 2523, 0913, T.Posner, and R.Hess, Chem. Ber., 46, 3816, 1913, M. Gianella, F. Gualtieri, C. Melchiorre and A. Orlandoni, Chem. Therap., 1972, 2, 127) and starts from 4-hydroxy-coumarin in the reaction with metallic sodium as shown in the following scheme 2:

Scheme 2

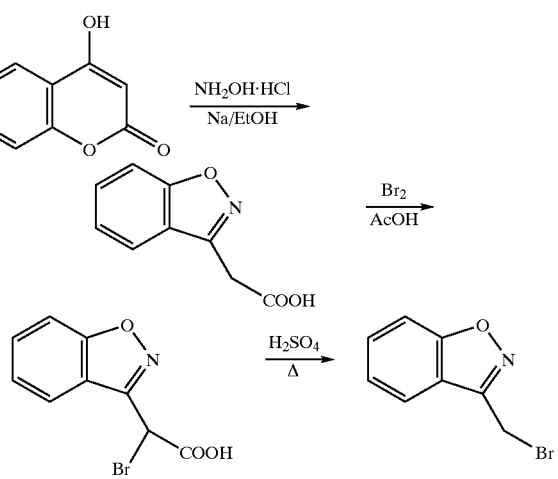

The Posner reaction for BOA preparation involves the use of metallic sodium. When metallic sodium is used in alcoholic solution, BOA is not the sole reaction product and the side-reaction product, O-hydroxy-acetophenone-oxime, is obtained in about 30%.

The high percentage of the side reaction products as well as the difficulty of using the aforementioned process on an industrial scale due to the use of metallic sodium render said process unfavorable, and thus the need for an improved process for preparing BOA and BOS—Na intermediates remains.

According to Dainnipon in the patent Japanese Pat. No. 53-77057, an alternative synthetic route for preparing zonisamide starts from 4-hydroxy-coumarin may occur via the same intermediates BOA and BOS—Na as shown in the following scheme 3:

Scheme 3

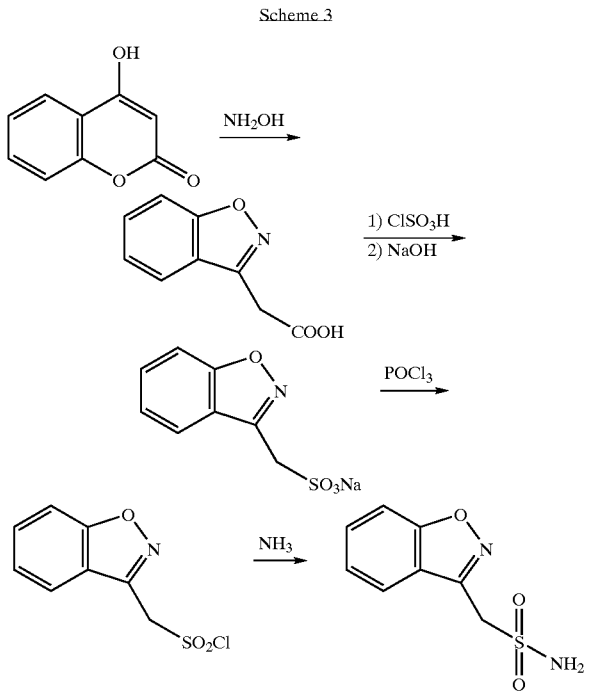

1,2-benzizoxazole-3-acetic acid (BOA), the product of the initial step after reacting 4-HC with $NH_{20}H$ (scheme 3), is converted to the intermediate BOS—Na in the sulfonation reaction with $ClSO_3H$/dioxane in ethylene chloride at room temperature for about three hours followed by about 6 hours heating at about 50° C. After the reaction is complete, water and NaOH are added and the product is isolated as sodium salt (BOS—Na) by evaporation of the aqueous layer. BOA and BOS—Na are the intermediates in the zonisamide preparation according to both synthetic schemes. All the cited references are incorporated by reference in their entireties herein.

OBJECTS AND SUMMARY OF THE INVENTION

An object of the present invention is to provide an improved process for preparing a salt of BOS (e.g., BOS—Na) with higher purity and lesser side-products.

Another object of the present invention is to provide an improved process for preparing a salt of BOS (e.g., BOS—Na) as an intermediate for the preparation of 1,2-benzisoxazole-3-methane sulfonamide (i.e., zonisamide).

Another object of the present invention is to provide an improved process for preparing a salt of BOS (e.g., BOS—Na) in which the sulfonation of BOA occurs in a solvent of methylene chloride (instead of ethylene chloride).

Another object of the present invention is to prepare 1,2-benzisoxazole-3-acetic acid (BOA) without the use of metallic sodium; and thus the process of this invention is substantially less hazardous.

Another object of the present invention is to prevent the formation of side-products, e.g., oximes; and thus, significantly increasing the yield of BOA, and substantially reducing the burden of removing the oxime side-product with ether, which by itself is hazardous.

Another yet object of the present invention is to prepare BOA or salts of BOS (e.g., BOS—Na); which are thereafter converted to 1,2-benzisoxazole-3-methane sulfonamide (i.e., zonisamide).

The present invention provides a process for preparing 1,2-benzisoxazole-3-acetic acid (BOA), comprising the step of reacting 4-hydroxy-coumarin (4-HC) with hydroxyl-amine in the presence of a base.

In a preferred embodiment, the base is selected from the group consisting of carbonate salts, aqueous ammonia, and organic bases. In another preferred embodiment, the carbonate salt is selected from the group of sodium carbonate ($Na_2CO_3$) and potassium carbonate ($K_2CO_3$). In another preferred embodiment, the organic base is an amine. More preferably, the amine is selected from the group consisting of triethyl-amine, tributyl-amine, and diethyl-amine.

In another preferred embodiment, the present invention provides a process for preparing 1,2-benzisoxazole-3-acetic acid (BOA), comprising the step of reacting 4-hydroxy-coumarin (4-HC) with hydroxyl-amine in the presence of a base, said process occurs in the presence of an alcoholic solvent.

Preferably, the alcoholic solvent is a lower alcohol. More preferably, the lower alcohol is selected from the group consisting of ethanol, methanol, n-butanol, iso-propyl-alcohol, iso-butanol, amyl-alcohol, and iso-amyl-alcohol.

In another preferred embodiment, the present invention provides a process for preparing 1,2-benzisoxazole-3-acetic acid (BOA), comprising the step of reacting 4-hydroxy-coumarin (4-HC) with hydroxyl-amine in the presence of a base and an alcoholic solution, wherein said process occurs at a temperature between room temperature and boiling point of the alcoholic solvent.

More preferably, the temperature of the reaction is between about 40° C. and about 60° C.

The present invention also provides an improved process of preparing a salt of benzisoxazole methane sulfonic acid, comprising the steps of: 1) sulfonating 1,2-benzisoxazole-3-acetic acid (BOA) using chlorosulfonic acid and dioxane in methylene chloride and sodium hydroxide solvents; and 2) isolating the salt of benzisoxazole methane sulfonic acid.

The present invention provides an improved process for preparing a salt of BOS (e.g., BOS—Na) in which the product is isolated by precipitatation from an aqueous solvent. Preferably, the precipitation is performed by salting-out with, e.g., sodium chloride. More preferably, the precipitation is performed by salting-out and and cooling.

In another preferred embodiment, the salt of BOS (e.g., BOS—Na) is isolated by evaporation.

Preferably, the salt of BOS may be isolated as BOS-Ba or BOS—Ca.

In another preferred embodiment, the preparation of the BOS-salt (e.g., BOS—Na) occurs at about 40° C., preferably at about 55° C. Preferably, the preparation of the BOS-salt is performed for a time duration of about 4 hours. More preferably, the preparation is performed for about 3, about 3.5 and about 5 hours.

According to the present invention, the reaction was improved as the reaction (for converting BOA to BOS—Na) is faster when methylene chloride is used. In other words, the reaction rate is faster when the solvent of the reaction is changed from ethylene chloride to methylene chloride.

DETAILED DESCRIPTION OF THE INVENTION

As used herein, the following abbreviations are used: 1,2-benzisoxazole-3-acetic acid (BOA); benzisoxazole methane sulfonic acid (BOS); sodium salt of benzisoxazole methane sulfonic acid (BOS—Na); barium salt of benzisoxazole methane sulfonic acid (BOS-Ba); calcium salt of benzisoxazole methane sulfonic acid (BOS—Ca), chlorosulfonic acid ($ClSO_3H$); "organic base" refers to a base of carbon compounds; "room temperatuer" refers to ambient temperature of about 20° C. to about 25° C.

As disclosed in the present application, when methylene chloride was used to repeat the procedure as disclosed in Japanese Patent 53-77057, it was found that the reaction was substantially faster. The reaction was completed in about 12–17 hours of heating when ethylene chloride was used. In contrast, the reaction was completed in only about 3–5 hours at about 40° C. when methylene chloride was used (See, the exp. #2337 and exp. #2356 in the Table 1).

According to the present invention, the process was further improved as it provides an alterative isolation procedure. It is known that the product (BOS—Na) can be isolated by evaporation of an aqueous phase. The present invention also provides two alternatives in which the product is precipitated from water which can be induced by the following ways; for example:

a) BOS—Na may be isolated from water by precipitation by salting-out; e.g., with sodium chloride (i.e., NaCl) and cooling; and b) BOS-Ba or BOS—Ca may be isolated based on their low solubility, and can be quantitatively precipitated from water. Separation of BOS as the barium (Ba) or calcium (Ca) salt facilitates industrial scale preparation of this intermediate. Once the salt precipitates, it may be washed with water to reduce the inorganic salt content.

A product contaminated with inorganic salts is usually more hygroscopic than the pure compound; and, its use is problematic in the $POCl_3$ reaction.

EXAMPLES

The present invention is described below in detail with reference to examples. The present invention is by no means restricted to these specific examples. The experiments are summaried as followed.

TABLE 1

BOS Preparation Experiments

| Exp. | Solvent | Temp. (° C.) | Reaction time (hours) | Salt type | Isolation of the product Procedure | Reference |
|---|---|---|---|---|---|---|
| # 2337 | $C_2H_4Cl_2$ (ethylene chloride) | 55° C. | 12 | Na | Evaporation of the water solution | Process as in JP 53-77057 |
| # 2356 | $CH_2Cl_2$ (methylene chloride) | 40° C. | 4 | Na | Evaporation of the water solution | Present process |
| # 2361 | $CH_2Cl_2$ | 40° C. | 5 | Na | Precipitation from water by salting-out with NaCl | Present process |
| # 2362 | $CH_2Cl_2$ | 40° C. | 3 | Ca | Precipitation from water | Present process |
| # 2363 | $CH_2Cl_2$ | 40° C. | 3.5 | Ba | Precipitation from water | Present process |

TABLE 2

% BOA Yield and % Side-Products Under Various Experimental Conditions

| Exp. No. | Solvent | Base | BOA Yield (%) | % Oxime | % Unreacted 4-HC | Reference |
|---|---|---|---|---|---|---|
| 1 | Ethanol | Na | 68.3 | 19.8 | | 1 |
| 2 | Ethanol-water | Na-acetate | 48.7 | 30.8 | | 2 |
| 3* | Ethanol | $Na_2CO_3$ | 82 | 0.2 | 17.5 | Present procedure |
| 4* | Methanol | $Na_2CO_3$ | 87.5 | 1.1 | 7.5 | Present procedure |
| 5* | n-BuOH | $Na_2CO_3$ | 98 | 0.9 | 1 | Present procedure |
| 6* | n-BuOH | $K_2CO_3$ | 82.9 | 17 | | Present procedure |

*% represents area of HPLC chromatogram of respective products over total area
Reference 1: Chem. Pharm. Bull., (Tokyo), 24, 632, 1976 T. Posner and R. Hess, Ber., 46, 3816, 1913
Reference 2: G. Casisni, F. Gualtieri, M.L. Stern, J. Hererocyclic Chem., 2, 385, 1965

Experimental Procedures

Example 1

Reaction with $Na_2CO_3$/n-BuOH

4-Hydroxy-coumarin (10 grams), was added to the mixture of hydroxyl-amine hydrochloride (15 grams) and sodium carbonate (23 grams) in n-BuOH (100 mL). The reaction mixture was than heated to reflux and the reflux was maintained for about 13 hours. The reaction mixture was concentrated on rotavapor and the residue was washed with water and dried at about 60° C. The product weighs about 8.56 grams (yield: about 80% w/w).

Example 2

Reaction with $K_2CO_3$/n-BuOH

4-Hydroxy-coumarin (10 grams) was added to the mixture of hydroxyl-amine hydrochloride (15 grams) and potassium carbonate (9.30 grams) in n-BuOH (100 mL). The reaction mixture was heated at reflux for about 20 hours.

The HPLC analysis of the reaction mixture shows the following composition: about 80% product BOA (w/w), about 15% oxime (w/w) and about 5% 4-HC (w/w).

Example 3

Reaction with $Et_3N/MeOH$

4-Hydroxy-coumarin (10 grams), hydroxyl-amine hydrochloride (15 grams) and triethyl-amine (22 grams) in MeOH (50 mL) were heated at reflux for about 1.5 hours. The residue obtained after evaporation to dryness was dissolved in aqueous $NaHCO_3$ and extracted with ether. After acidification of the aqueous phase the product was isolated by filtration and washed with water. The yield is about 73% (w/w).

Example 4

Reaction with $Et_2NH/MeOH$

4-Hydroxy-coumarin (100 grams), hydroxyl-amine hydrochloride (150 grams) and diethyl-amine (160 grams) in MeOH (500 mL) were heated at reflux for about 1 hour. The reactiom mixture was evaporated to dryness and the solid was dissolved in aqueous. $NaHCO_3$ and extracted with ether; from the aqueous phase the product was obtained upon acidification with HCl. The solid was washed with water and dried on oven at about 60° C. The solid weighs about 99.82 grams (yield: about 93% w/w).

It is contemplated that various modifications of the described modes of carrying out the invention will be apparent to those skilled in the ar without departing from the scope and spirit of the invention.

What is claimed is:

1. A process of preparing a salt of benzisoxazole methane sulfonic acid comprising the steps of: 1) sulfonating 1,2-benzisoxazole-3-acetic acid using chlorosulfonic acid and dioxane in a solvent mixture comprising methylene chloride and sodium hydroxide; and 2) isolating the salt of benzisoxazole methane sulfonic acid.

2. The process according to claim 1, wherein the isolating step is performed by evaporating the solvent mixture after the sulfonating step.

3. The process according to claim 1, wherein the isolating step is performed by salting-out with sodium chloride.

4. The process according to claim 3, further comprising the step of cooling after the step of salting-out.

5. The process according to claim 1, wherein the salt of benzisoxazole methane sulfonic acid is selected from the group consisting of sodium, calcium, and barium.

6. The process according to claim 1, wherein the preparation of benzisoxazole methane sulfonic acid is performed at a temperature of about 40° C. and for a time of about 4 hours.

7. The process according to claim 1, wherein the preparation of benzisoxazole methane sulfonic acid is performed at a temperature of about 40° C. and a time of about 5 hours.

8. The process according to claim 1, wherein the preparation of benzisoxazole methane sulfonic acid is performed at a temperature of about 40° C. and a time of about 3 hours.

9. The process according to claim 1, wherein the preparation of benzisoxazole methane sulfonic acid is performed at a temperature of about 55° C. and a time of about 3.5 hours.

10. The process according to claim 1, wherein the benzisoxazole methane sulfonic acid is thereafter converted to 1,2-benzisoxazole-3-methane sulfonamide.

11. 1,2-benzisoxazole-3-methane sulfonamide prepared in accordance with the process of claim 1.

12. The process according to claim 1, wherein the isolating step is performed by precipitation from water.

13. The process according to claim 12, wherein the precipitation is performed in the presence of a barium salt.

14. The process according to claim 12, wherein the precipitation is performed in the presence of a calcium salt.

15. The process according to claim 1, wherein the 1,2-benzisoxazole-3-acetic acid is selectively sulfonated to form the salt of benzisoxazole methane sulfonic acid in the sulfonating step.

16. The process according to claim 15, wherein the salt of benzixazole methane sulfonic acid has high purity.

* * * * *

UNITED STATES PATENT AND TRADEMARK OFFICE
CERTIFICATE OF CORRECTION

PATENT NO. : 6,677,458 B2
DATED : January 13, 2004
INVENTOR(S) : Mendelovici et al.

It is certified that error appears in the above-identified patent and that said Letters Patent is hereby corrected as shown below:

Title page,
Item [56], References Cited, U.S. PATENT DOCUMENTS, please add:
-- 4,172,896  10/1979 Uno et al. --

OTHER PUBLICATIONS, please add the following references:
-- M. Shimizu et al., "Research and Development of Zonisamide, a New Type of Antiepileptic Drug," Yakugaku Zasshi, Vol. 116, No. 7, July 1996, pp. 533-47

H. Uno et al., "Studies on 3-Bustituted 1,2-Benzisoxazole Derivatives," Chem. Pharm. Bull. (Tokyo), Vol. 24, No. 4, January 1976, pp. 632-643

M. Giannella et al., "Aminoacids with 1,2-benzisoxazole nucleus: D,L-(1-2-benzisoxazole-3) glycine, D,L-β-(1-2-benzisoxazole-3) alanine and analogues (*)," Chem. Therap., Vol. 7., No. 2, March-April 1972, pp. 127-132

G. Casini et al., "On 1,2-Benzisoxazole-3-acetic Acid (1)," Heterocyclic Chem., Vol. 2, No. 4, December 1965, 385-386 --

Column 1,
Line 11, change "the disclosure of which is incorporated by reference in its" to
-- the disclosures of which are incorporated by reference in their --;
Line 26, change "avaiable" to -- available --;
Line 27, change "convulant" to -- convulsant --;

Column 2,
Line 27, change "benzizoxazole" to -- benzisoxazole --;
Line 66, change "Dainnipon" to -- Dainippon --;
Line 66, change "in the patent Japanese Pat. No." to -- in the Japanese Pat. No. --;

Column 3,
Line 1, change "coumarin may occur" to -- coumarin and may occur --;
Line 33, change "benzizoxazole" to -- benzisoxazole --;
Line 57, change "occurs in a solvent of methylene" to -- occurs in methylene --;
Line 67, change "which by itself" to -- which itself --;

Column 4,
Line 1, change "Another yet object" to -- Yet another object --;

Column 5,
Line 6, change "temperatuer" to -- temperature --;
Line 53, change "alterative" to -- alternative --;

UNITED STATES PATENT AND TRADEMARK OFFICE
CERTIFICATE OF CORRECTION

PATENT NO.    : 6,677,458 B2
DATED         : January 13, 2004
INVENTOR(S)   : Mendelovici et al.

It is certified that error appears in the above-identified patent and that said Letters Patent is hereby corrected as shown below:

Column 6,
Line 13, change "summaried as followed" to -- summarized as follows --;
Line 47, change "Casisni" to -- Casini --;
Line 47, change "Hererocyclic" to -- Heterocylic --;
Line 60, change "concentrated on rotavapor" to -- concentrated by rotavapor --;

Column 7,
Line 27, change "aqueous.NaHCO$_3$" to -- aqueous NaHCO$_3$ --;
Line 30, change "dried on oven" to -- dried by oven --;
Line 34, change "skilled in the ar" to -- skilled in the art --;

Column 8,
Line 28, change "1,2-benzisoxazole-3-methane" to -- 1,2-Benzisoxazole-3-methane --;
Line 41, change "benzixazole" to -- benzisoxazole --.

Signed and Sealed this

Twenty-third Day of November, 2004

JON W. DUDAS
*Director of the United States Patent and Trademark Office*